(12) United States Patent
Feng et al.

(10) Patent No.: US 12,280,044 B2
(45) Date of Patent: Apr. 22, 2025

(54) PROTEOLYSIS-TARGETING CHIMERA MOLECULE AND PREPARATION METHOD AND USE THEREOF

(71) Applicant: GUANGZHOU MEDICAL UNIVERSITY, Guangdong (CN)

(72) Inventors: Du Feng, Guangdong (CN); Wei Yi, Guangdong (CN); Yongquan Hu, Guangdong (CN); Junyuan Tang, Guangdong (CN); Zhi Zhou, Guangdong (CN); Haixia Zhuang, Guangdong (CN)

(73) Assignee: GUANGZHOU MEDICAL UNIVERSITY, Guangzhou (CN)

( * ) Notice: Subject to any disclaimer, the term of this patent is extended or adjusted under 35 U.S.C. 154(b) by 0 days.

(21) Appl. No.: 18/426,321

(22) Filed: Jan. 29, 2024

(65) Prior Publication Data

US 2024/0245671 A1    Jul. 25, 2024

Related U.S. Application Data

(63) Continuation of application No. PCT/CN2023/092388, filed on May 5, 2023.

(30) Foreign Application Priority Data

Jul. 14, 2022  (CN) .......................... 202210830254.0

(51) Int. Cl.
*A61K 31/4545* (2006.01)
*A61K 8/49* (2006.01)
*A61Q 19/02* (2006.01)

(52) U.S. Cl.
CPC ........ *A61K 31/4545* (2013.01); *A61K 8/4933* (2013.01); *A61Q 19/02* (2013.01)

(58) Field of Classification Search
CPC .. C07D 213/44; C07D 213/52; C07D 209/48; A61K 31/4418; A61K 31/4545
See application file for complete search history.

(56) References Cited

U.S. PATENT DOCUMENTS 2,713,049 A * 7/1955 Bernstein ............. C07D 213/89
546/326

FOREIGN PATENT DOCUMENTS

| CN | 111909155 A | 11/2020 |
| CN | 113735824 A | 12/2021 |

OTHER PUBLICATIONS

Fu (European Journal of Medicinal Chemistry vol. 226 113830 published online Oct. 2, 2021) (Year: 2021).*
Xin-Yuan Sheng et al., Advances in the optimization of the linker in proteolysis-targeting chimeras (PROTAC), Acta Pharmaceutica Sinica, Dec. 31, 2021, pp. 445-455, vol. 56, No. 2.
Fangqing Zhang et al., Discovery of a new class of Protac BRD4 degraders based on a dihydroquinazolinone derivative and lenalidomide / pomalidomide, Bioorganic & Medicinal Chemistry, 2019, vol. 28.
Notice of Allowance of counterpart Chinese Patent Application No. 202210830254.0 issued on Mar. 30, 2023.
First Office Action of counterpart Chinese Patent Application No. 202210830254.0 issued on Mar. 8, 2023.

* cited by examiner

*Primary Examiner* — Clinton A Brooks
*Assistant Examiner* — George W Kosturko (57) ABSTRACT

The present application belongs to the technical field of proteolysis-targeting chimeras (PROTACs), and discloses a PROTAC molecule and a preparation method and use thereof. A ligand for a target protein in the PROTAC molecule of the present application is a pyridine carboxylic acid-1-oxide derivative. In cell and zebrafish experiments, the PROTAC molecule exhibits no toxic and side effects at a drug concentration allowing a desired effect. At a cellular level, an inhibition level of the PROTAC molecule for human tyrosinase (TYR) reaches less than or equal to 1 μmol/L. The PROTAC molecule in the present application can significantly reduce the generation of melanin by degrading TYR, and has excellent solubility, safety, and efficacy and a low effective concentration.

1 Claim, 12 Drawing Sheets

PROTEOLYSIS-TARGETING CHIMERA MOLECULE AND PREPARATION METHOD AND USE THEREOF

CROSS-REFERENCE TO RELATED APPLICATIONS

The present application is a continuation application of PCT application No. PCT/CN2023/092388 filed on May 5, 2023, which claims the benefit of Chinese Patent Application No. 202210830254.0 filed on Jul. 14, 2022. The contents of all of the aforementioned applications are incorporated by reference herein in their entirety.

TECHNICAL FIELD

The present application relates to the technical field of proteolysis-targeting chimeras (PROTACs), and specifically to a PROTAC molecule and a preparation method and use thereof.

BACKGROUND

In 2020, the medical beauty industry has a market scale of 197.5 billion yuan. Skin whitening is one of the key concerns of the medical beauty industry, and the development of safe and effective whitening agents has important economic values and significance.

Tyrosinase (TYR) is a key rate-limiting enzyme for melanocytes to produce melanin, and thus the direct inhibition of catalytic activity of TYR is the most prominent and effective target. Most of the cosmetics or whitening agents on the market are TYR inhibitors. Many TYR inhibitors such as hydroquinone (HQ), arbutin, kojic acid, azelaic acid, L-ascorbic acid, and a resorcinol derivative have been used as whitening agents, but show defects such as cytotoxicity and easy failure. Specific situations are shown in Table 1.

TABLE 1

| Mechanisms and defects of whitening ingredients | | |
|---|---|---|
| Whitening ingredient | Mechanism | Defects |
| HQ | HQ works by inhibiting activity of TYR. | HQ is highly cytotoxic and has been banned. |
| Kojic acid | Kojic acid works by competitively inhibiting activity of TYR. | Kojic acid is a sensitizing agent and may cause a cell mutation. |
| Arbutin | Arbutin works by inhibiting activity of TYR. | Arbutin is highly concentration-dependent and cytotoxic, has unstable chemical properties, and may be hydrolyzed to produce HQ. |
| Retinoid | Retinoid works by inhibiting TYR and interfering with the transfer of a pigment. | Retinoid is highly concentration-dependent and may induce irritant dermatitis. |
| Resveratrol | Resveratrol works by competitively inhibiting the oxidation of TYR for L-tyrosine. | Resveratrol is highly concentration-dependent, and exhibits an inferior whitening effect to HQ, kojic acid, arbutin, or the like. |
| Azelaic acid | Azelaic acid works by competitively inhibiting activity of TYR. | Azelaic acid is highly concentration-dependent, and causes an allergy to some people. |
| Licorice extract | Licorice extract works as an anti-inflammatory factor, and can decompose melanin. | Licorice extract is effective merely at a high dose and is expensive. |
| Ascorbic acid | Ascorbic acid works by reducing the production of DQ and preventing the oxidation of DHICA. | Ascorbic acid alone does not play a significant role, has unstable chemical properties, and is easily oxidized. |
| Soybean protein | Soybean protein works by inhibiting the transport of melanosomes. | Soybean protein exhibits an inferior whitening effect to whitening agents such as HQ. |
| Nicotinamide and analogues thereof | Nicotinamide and analogues thereof work by inhibiting the transport of melanosomes. | Nicotinamide and analogues thereof are teratogenic and intolerant to some populations. |
| Thujaplicin | Thujaplicin works by efficiently inhibiting TYR. | Thujaplicin is allergenic and irritant, and is generally used as a preservative. |
| Resorcinol derivative | Resorcinol derivative works by efficiently inhibiting TYR. | The use of a resorcinol derivative is restricted. |

A PROTAC technology is a drug development technology where an ubiquitin-proteasome system (UPS) is used to degrade a target protein. Compared with the traditional drugs, PROTACs have advantages such as small dose, independence on an affinity, high selectivity, and clearance of protein accumulation, and can overcome the drug resistance caused by mutation/overexpression of a target protein. Therefore, it is necessary to develop a TYR inhibitor by a PROTAC technology.

SUMMARY

An objective of the present application is to overcome the deficiencies of the prior art and provide a PROTAC molecule and a preparation method and use thereof.

In order to allow the above objective, the present application adopts the following technical solutions:

In a first aspect, the present application provides a PROTAC molecule, where a ligand for a target protein in the PROTAC molecule is a pyridine carboxylic acid-1-oxide derivative.

In cell and zebrafish experiments, the PROTAC molecule of the present application exhibits no toxic and side effects at a drug concentration allowing a desired effect. At a cellular level, an inhibition level of the PROTAC molecule for human TYR reaches less than or equal to 1 μmol/L. When zebrafish embryos and juvenile fish each are treated with the PROTAC molecule at a concentration of 1 μmol/L, the PROTAC molecule is significantly different from a positive control in terms of melanin production. That is, the PROTAC molecule of the present application can significantly reduce the production of melanin by degrading TYR, and has excellent solubility, safety ($IC_{50}$>200 μM), and efficacy and a low effective concentration (1 μM to 10 μM).

As a preferred embodiment of the PROTAC molecule provided in the present application, a structural formula of the pyridine carboxylic acid-1-oxide derivative is shown in formula (I):

formula (I)

where $R_1$ is a hydrogen bond, $R_2$ is hydroxyl or a hydrogen bond, and $R_3$ is mercapto.

As a preferred embodiment of the PROTAC molecule provided in the present application, a ligand in the PROTAC molecule to bind to an E3 ubiquitin ligase is synthesized with thalidomide or lenalidomide.

As a preferred embodiment of the PROTAC molecule provided in the present application, a structural formula of the PROTAC molecule is any one selected from the group consisting of formulas (II) to (IV):

formula (II)

where $R_1$ is H or OH, n is 2 to 8, and Y is $CH_2$ or CO;

formula (III)

where $R_1$ is H or OH, n is 2 to 8, X is O, and Y is $CH_2$ or CO; and formula (IV)

where $R_1$ is H or OH, n is 2 to 8, and Y is $CH_2$ or CO.

In a second aspect, the present application provides a preparation method of the PROTAC molecule, including the following steps:

(1) mixing a pyridine carboxylic acid-1-oxide derivative, 1-(3-dimethylaminopropyl)-3-ethylcarbodiimide hydrochloride (EDCI), 4-dimethylaminopyridine (DMAP), and N,N-dimethylformamide (DMF) to obtain a reaction solution a;

(2) adding thalidomide or lenalidomide to the reaction solution a, and allowing a complete reaction to obtain a reaction solution b;

(3) adding hydrochloric acid and ethyl acetate to the reaction solution b, and allowing extraction to obtain an organic phase; and (4) drying the organic phase.

As a preferred embodiment of the preparation method of the PROTAC molecule provided in the present application, the pyridine carboxylic acid-1-oxide derivative is 1-hydroxy-2-thio-1,2-dihydropyridine-4-carboxylic acid or 2-thio-1,2-dihydropyridine-4-carboxylic acid.

In a third aspect, the present application provides a TYR inhibitor including the PROTAC molecule.

In a fourth aspect, the present application provides use of the PROTAC molecule, the preparation method, or the TYR inhibitor in a whitening agent, a cosmetic, or a drug for treating a skin disease.

As a preferred embodiment of the use provided in the present application, the drug includes the PROTAC molecule and at least one pharmaceutically acceptable carrier.

As a preferred embodiment of the use provided in the present application, the drug is at least one selected from the group consisting of an oral preparation, an injection, an aerosol, and an ointment.

Compared with the prior art, the present application has the following beneficial effects:

In cell and zebrafish experiments, the PROTAC molecule of the present application exhibits no toxic and side effects at a drug concentration allowing a desired effect. At a cellular level, an inhibition level of the PROTAC molecule for human TYR reaches less than or equal to 1 μmol/L. That is, the PROTAC molecule of the present application can significantly reduce the production of melanin by degrading TYR, and has excellent solubility, safety ($IC_{50}$>200 μM), and efficacy and a low effective concentration (1 μM to 10 μM). The PROTAC molecule of the present application can be widely used in a whitening agent, a cosmetic, or a drug for treating a skin disease.

DETAILED DESCRIPTION

Figure 1A:
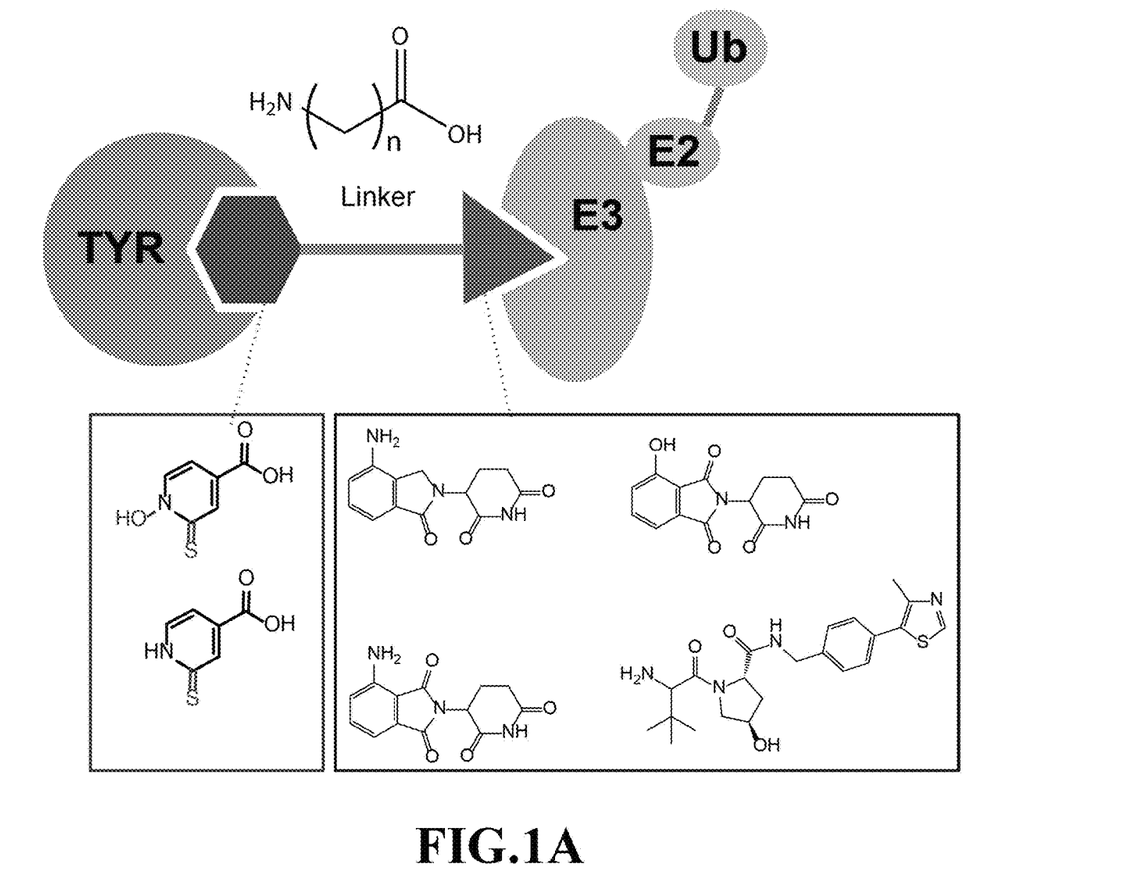
FIG. 1A shows a design of a PROTAC molecule.
Figure 1B:
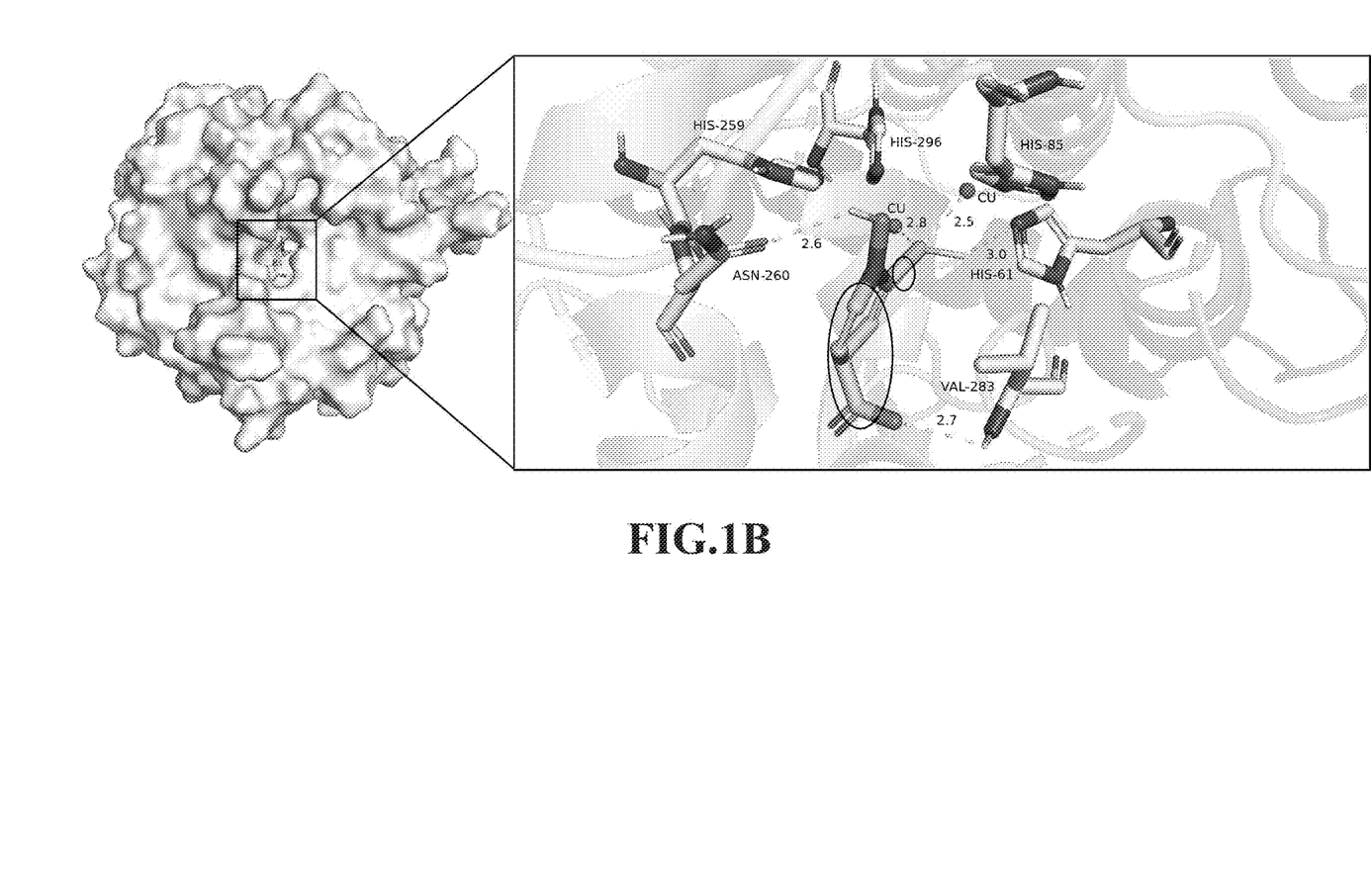
FIG. 1B shows a binding mode of TYR with S1, where surface representation of the crystal structure of TYR (PDB ID:2Y9X) in complex with S1 (the ellipses) is provided.
Figure 1C:
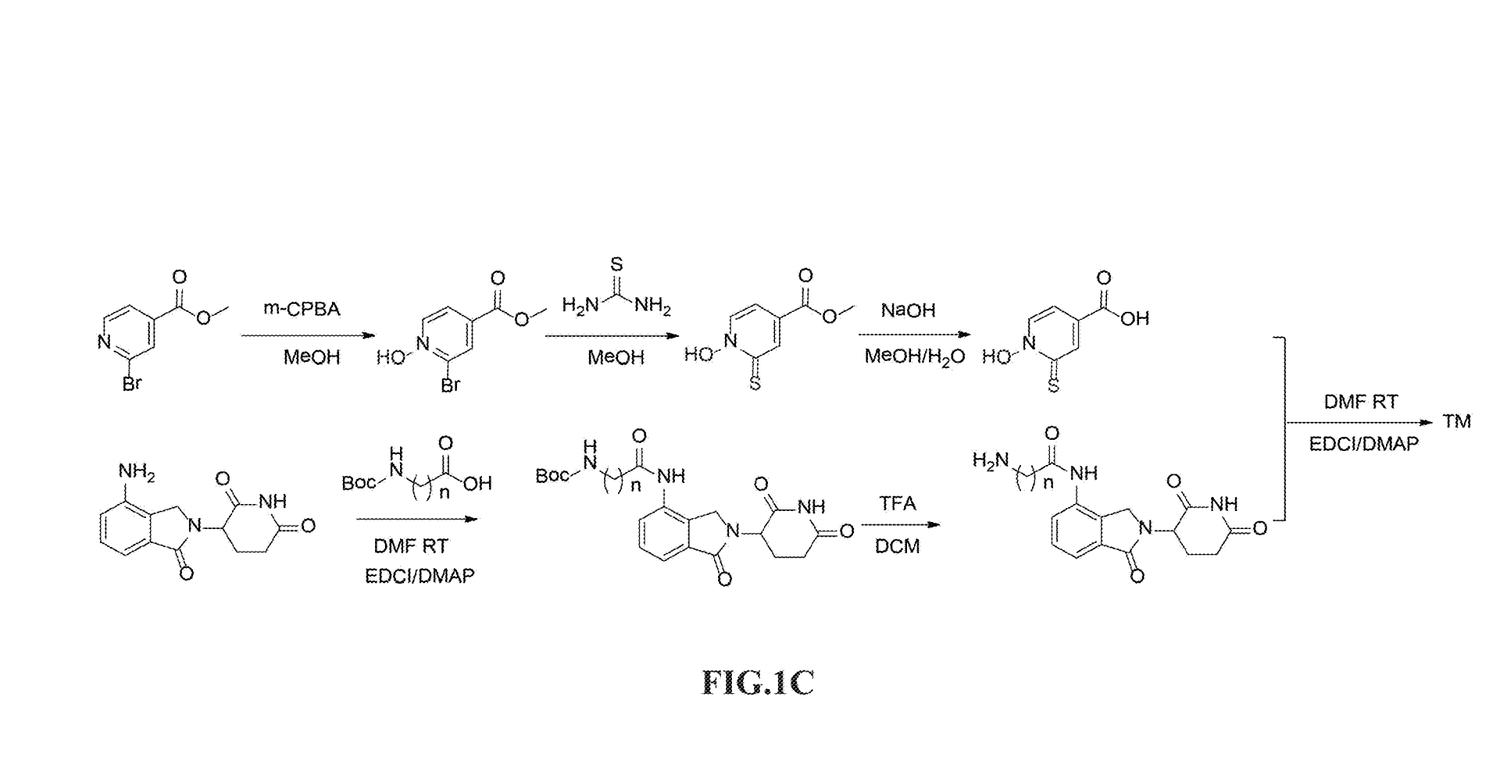
FIG. 1C shows a chemical synthesis route of a PROTAC molecule.

A design of the PROTAC molecule of the present application is shown in FIG. 1A. A small-molecule element in the PROTAC molecule to bind to TYR is a pyridine carboxylic acid-1-oxide derivative named S1. S1 is a small-molecule inhibitor for TYR and can directly bind to a TYR protein, and a molecular docking simulation diagram is shown in FIG. 1B. A ligand to bind to an E3 ubiquitin ligase is thalidomide (CAS No: 50-35-1) or lenalidomide (a derivative of thalidomide) (CC-5013) (CAS No: 191732-72-6), and thalidomide and lenalidomide both are ligands for the E3 ubiquitin ligase (cereblon, CRBN) used in synthesis of PROTAC. A chemical synthesis route of the PROTAC molecule is shown in FIG. 1C.

To well explain the objective, technical solutions, and advantages of the present application, the present application will be further explained below with reference to specific examples. It should be understood by those skilled in the art that the specific examples described herein are merely intended to explain the present application, rather than to limit the present application.

In the examples, unless otherwise specified, the experimental methods used are conventional, and the materials and reagents used are commercially available.

Example 1: Synthesis of A1

1-hydroxy-2-thio-1,2-dihydropyridine-4-carboxylic acid (0.2 mmol), EDCI (0.3 mmol), DMAP (CAS No: 25952-53-8) (0.24 mmol), and DMF (CAS No: 68-12-2) (2 mL) were added a reaction flask and stirred at room temperature for 5 min; then 7-amino-N-(2-(2,6-dioxopiperidin-3-yl)-1-oxoisoindolin-4-yl) heptanamide (0.22 mmol) was added, and when it was detected by thin layer chromatography (TLC) that a reaction was completed, 0.5 mol/L of hydrochloric acid (2 mL) was added to the reaction flask; extraction was conducted 3 times with ethyl acetate, and resulting organic phases were combined and spin-dried to obtain a crude product; and a target product A1 was prepared with the crude product through semi-preparative chromatography, where a structural formula of the target product A1 was shown in formula (V):

formula (V)

Example 2: Synthesis of A2

2-thio-1,2-dihydropyridine-4-carboxylic acid (0.2 mmol), EDCI (0.3 mmol), DMAP (0.24 mmol), and DMF (2 mL) were added to a reaction flask and stirred at room temperature for 5 min; then 5-amino-N-(2-(2,6-dioxopiperidin-3-yl)-1-oxo-isoindolin-4-yl) heptanamide (0.22 mmol) was added, and when it was detected by TLC that a reaction was completed, 0.5 mol/L of hydrochloric acid (2 mL) was added to the reaction flask; extraction was conducted 3 times with ethyl acetate, and resulting organic phases were combined and spin-dried to obtain a crude product; and a target product A2 was prepared with the crude product through semi-preparative chromatography, where a structural formula of the target product A2 was shown in formula (VI):

formula (VI)

Example 3: Synthesis of A3

2-thio-1,2-dihydropyridine-4-carboxylic acid (0.2 mmol), EDCI (0.3 mmol), DMAP (0.24 mmol), and DMF (2 mL) were added to a reaction flask and stirred at room temperature for 5 min; then 7-amino-N-(2-(2,6-dioxopiperidin-3-yl)-1-oxo-isoindolin-4-yl) heptanamide (0.22 mmol) was added, and when it was detected by TLC that a reaction was completed, 0.5 mol/L of hydrochloric acid (2 mL) was added to the reaction flask; extraction was conducted 3 times with ethyl acetate, and resulting organic phases were combined and spin-dried to obtain a crude product; and a target product A3 was prepared with the crude product through semi-preparative chromatography, where a structural formula of the target product A3 was shown in formula (VII):

formula (VII)

Example 4: Synthesis of B1

1-hydroxy-2-thio-1,2-dihydropyridine-4-carboxylic acid (0.2 mmol), EDCI (0.3 mmol), DMAP (0.24 mmol), and DMF (2 mL) were added to a reaction flask and stirred at room temperature for 5 min; then 4-((6-aminohexyl)oxy)-2-(2,6-dioxopiperidin-3-yl)isoindolin-1,3-dione (0.22 mmol) was added, and when it was detected by TLC that a reaction was completed, 0.5 mol/L of hydrochloric acid (2 mL) was added to the reaction flask; extraction was conducted 3 times with ethyl acetate, and resulting organic phases were combined and spin-dried to obtain a crude product; and a target product B1 was prepared with the crude product through semi-preparative chromatography, where a structural formula of the target product B1 was shown in formula (VIII):

formula (VIII)

Example 5: Synthesis of B2

2-thio-1,2-dihydropyridine-4-carboxylic acid (0.2 mmol), EDCI (0.3 mmol), DMAP (0.24 mmol), and DMF (2 mL) were added to a reaction flask and stirred at room temperature for 5 min; then 4-((6-aminohexyl)oxy)-2-(2,6-dioxopiperidin-3-yl)isoindolin-1,3-dione (0.22 mmol) was added, and when it was detected by TLC that a reaction was completed, 0.5 mol/L of hydrochloric acid (2 mL) was added to the reaction flask; extraction was conducted 3 times with ethyl acetate, and resulting organic phases were combined and spin-dried to obtain a crude product; and a target product B2 was prepared with the crude product through semi-preparative chromatography, where a structural formula of the target product B2 was shown in formula (IX):

formula (IX)

Test Example 1: Cell Experiment with a Human Melanoma Cell Line A375

The human melanoma cell line A375 was treated for 24 h with the molecule A3 at a concentration gradient, and then a protein sample was collected and tested by western blot (WB) to determine a protein level of TYR. In the concentration gradient, final concentrations of the molecule A3 were 0.001 μmol/L, 0.01 μmol/L, 0.1 μmol/L, 1 μmol/L, and 10 μmol/L, respectively.

Figure 2:
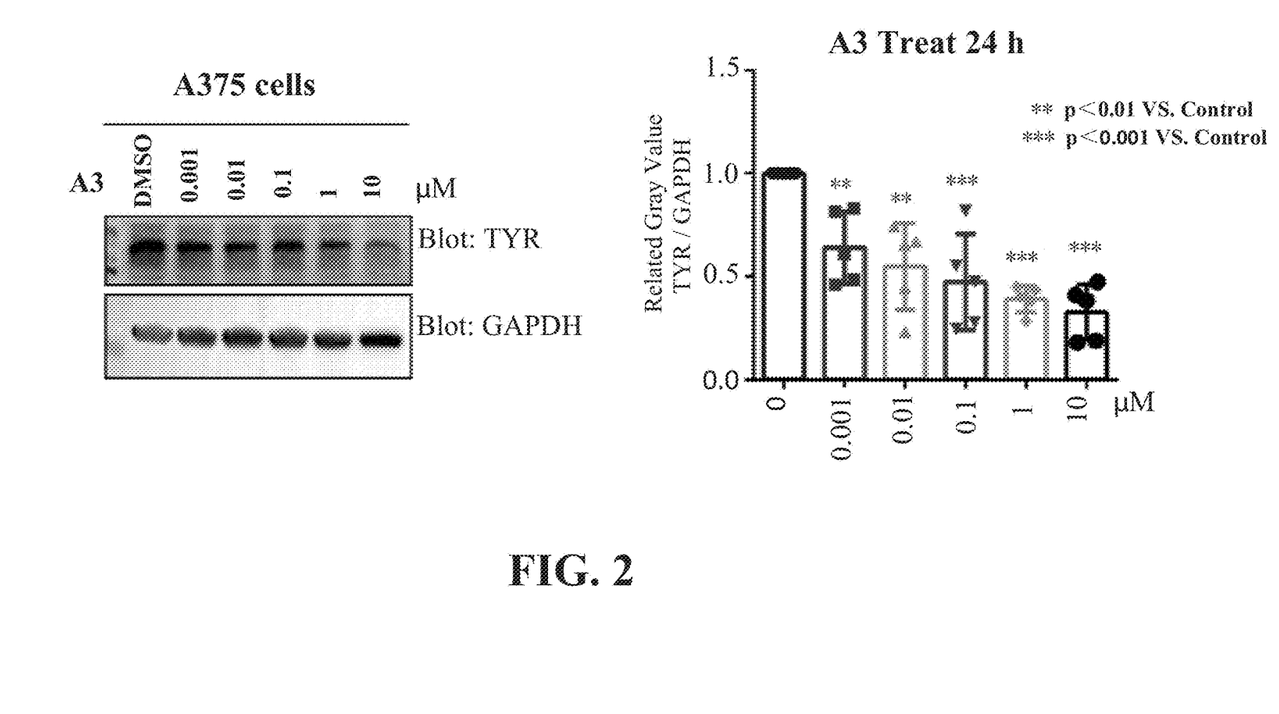
FIG. 2 shows an impact of treatment of a PROTAC molecule A3 on a TYR protein in a cell A375.

Results are shown in FIG. 2, and it can be seen that the molecule A3 has an inhibitory effect on TYR in the cell line A375, and the inhibitory effect of the molecule A3 on TYR in the cell line A375 is enhanced with the increase of a final concentration of the molecule A3.

Test Example 2: Cell Experiment with a Human Melanoma Cell Line MNT-1

The human melanoma cell line MNT-1 was treated for 24 h with the molecule A3 at a concentration gradient, and then a protein sample was collected and tested by WB to determine a protein level of TYR. In the concentration gradient, final concentrations of the molecule A3 were 0.001 μmol/L, 0.01 μmol/L, 0.1 μmol/L, 1 μmol/L, and 10 μmol/L, respectively.

Figure 3:
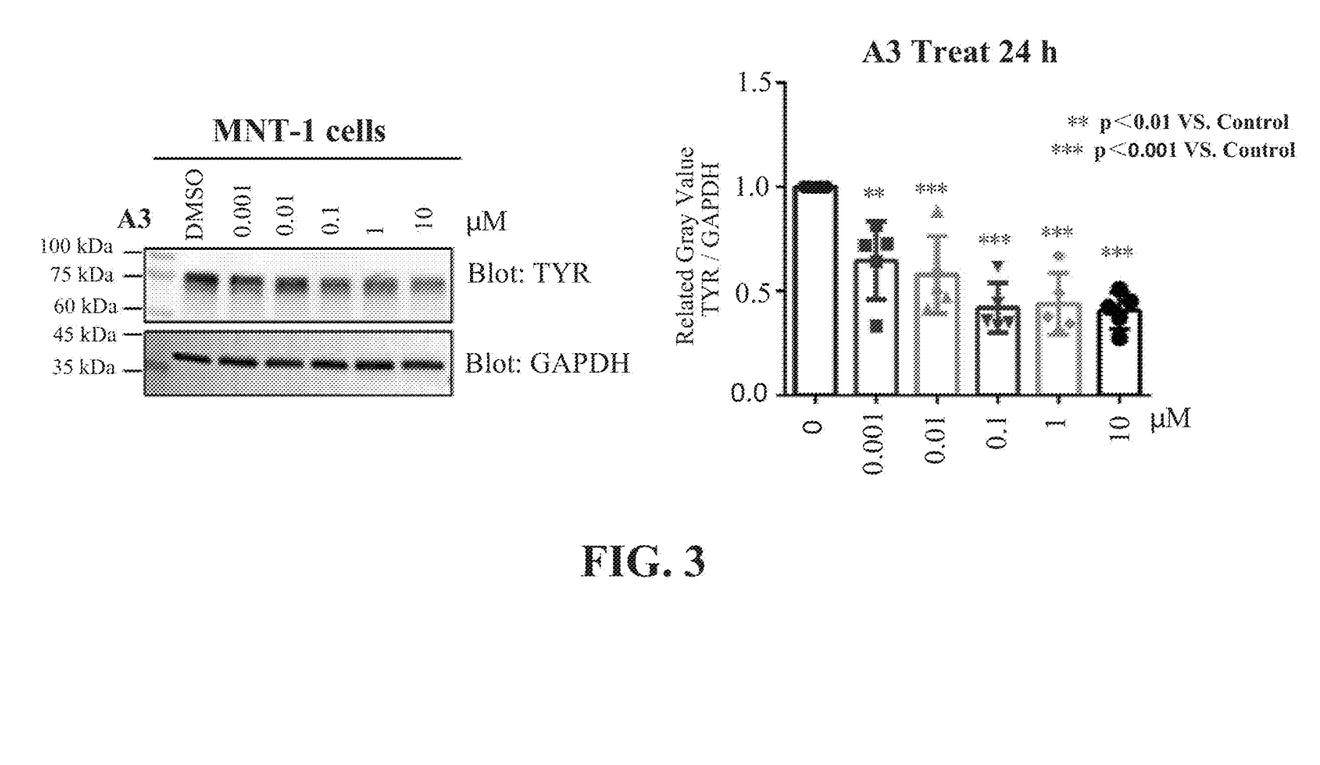
FIG. 3 shows an impact of treatment of a PROTAC molecule A3 on a TYR protein in a cell MNT-1.
Figure 4:
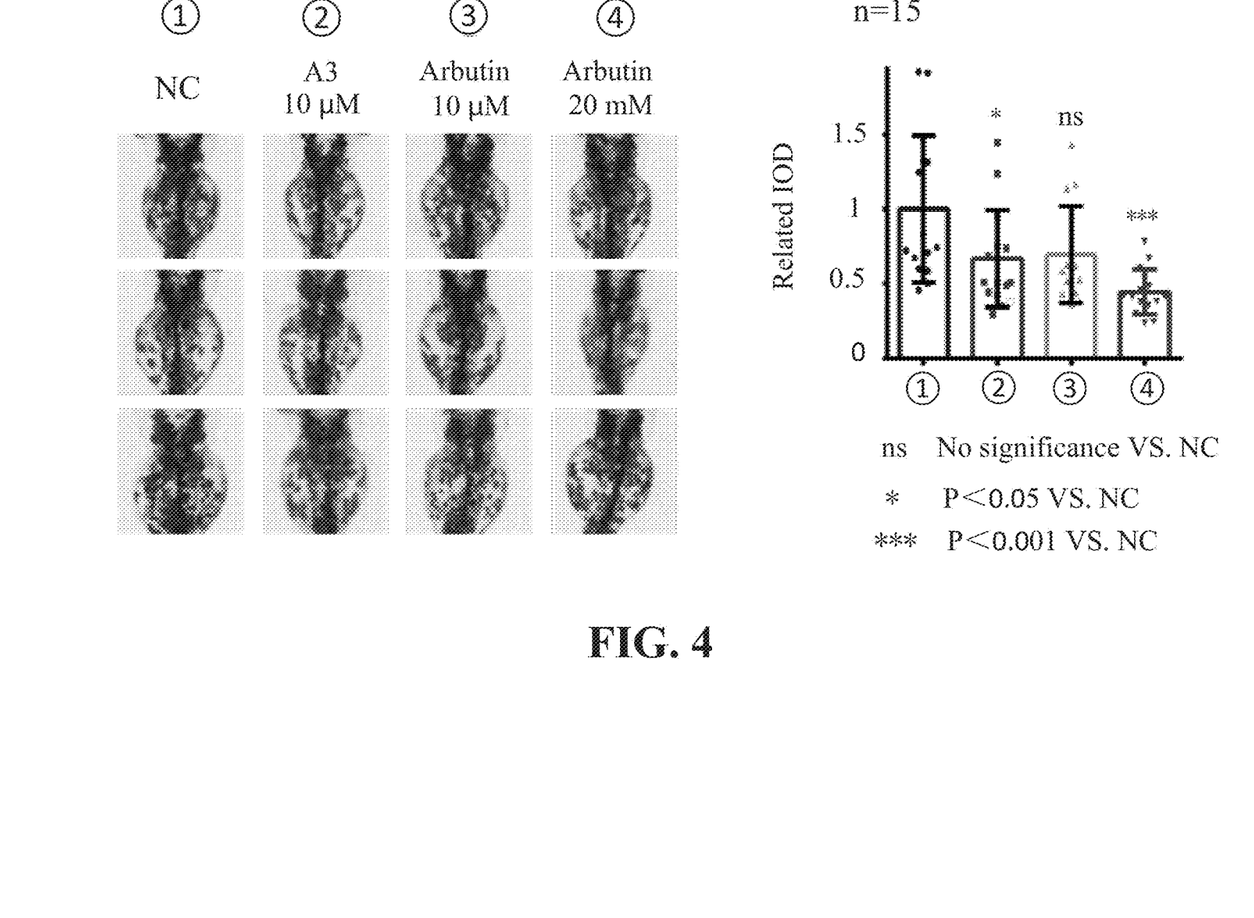
FIG. 4 shows an impact of a drug treatment on melanin production in a back of zebrafish (treatment time: 1 day)
Figure 5:
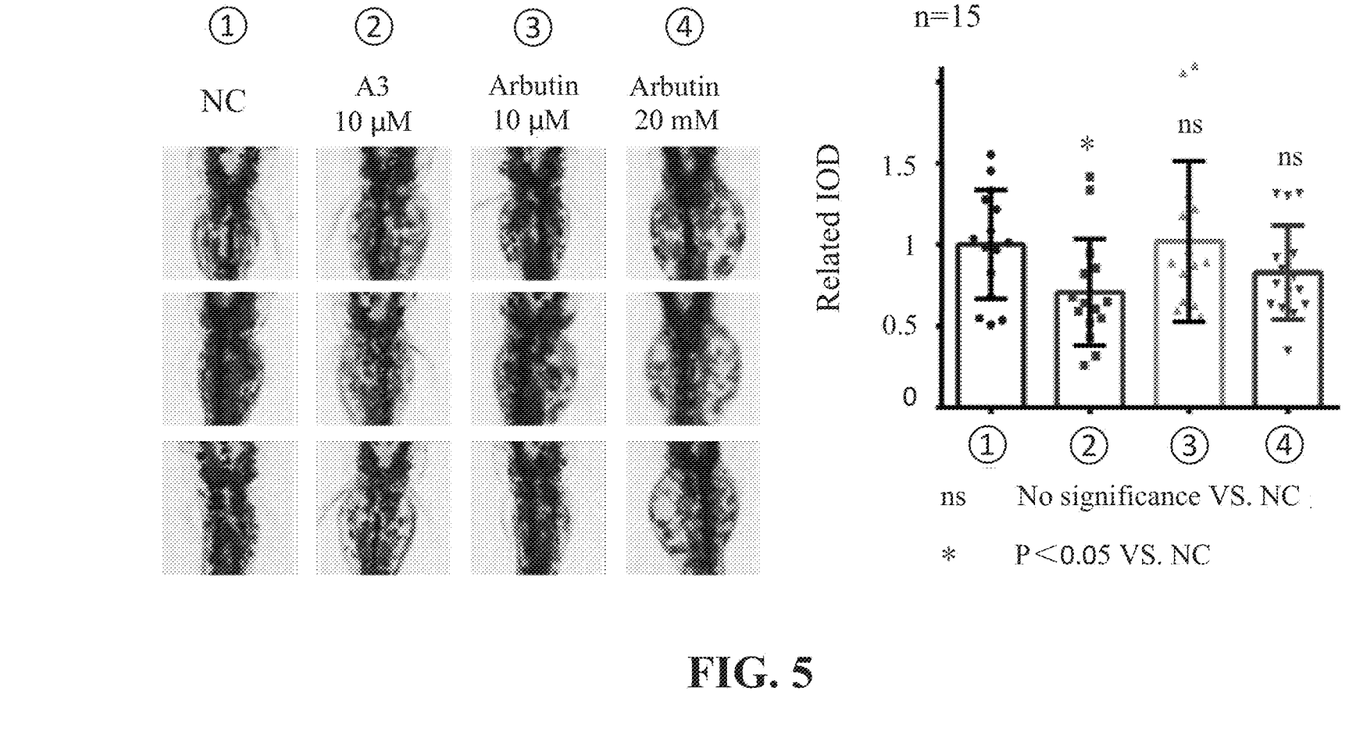
FIG. 5 shows an impact of a drug treatment on melanin production in a back of zebrafish (treatment time: 2 days)
Figure 6:
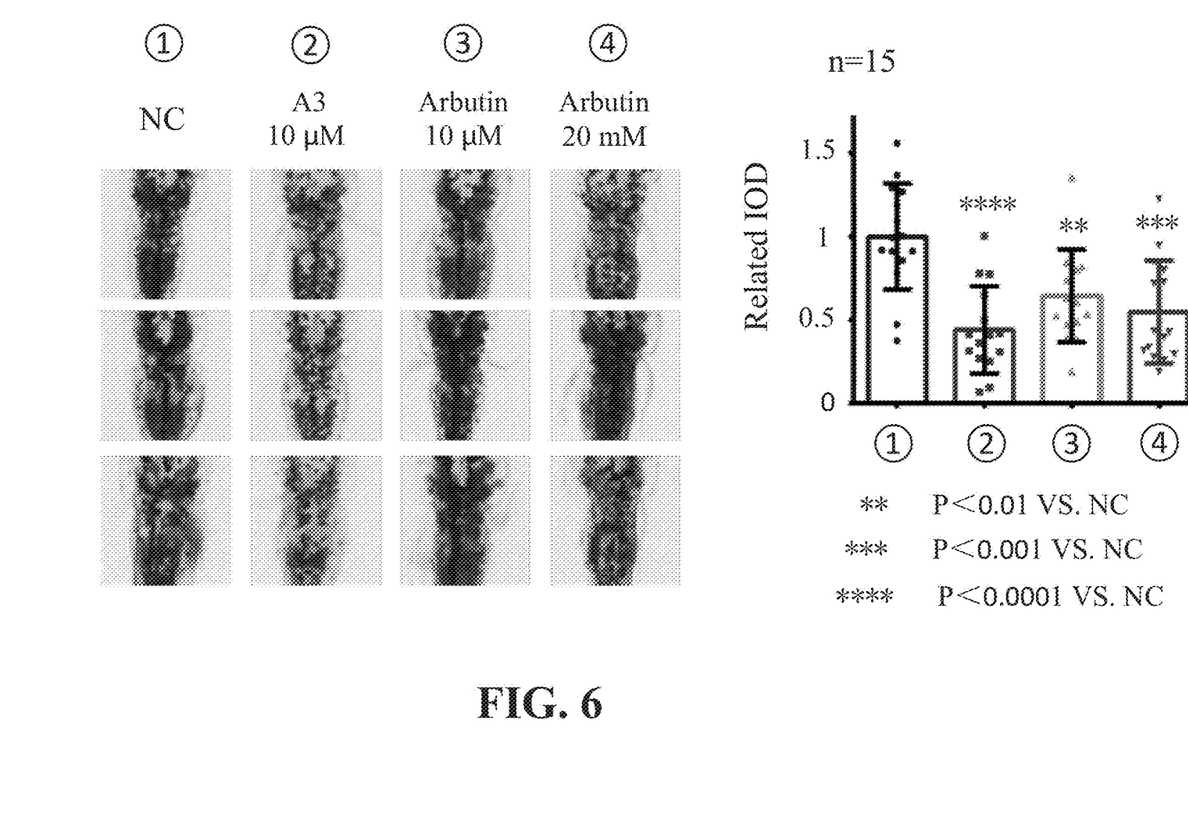
FIG. 6 shows an impact of a drug treatment on melanin production in a back of zebrafish (treatment time: 3 days)
Figure 7:
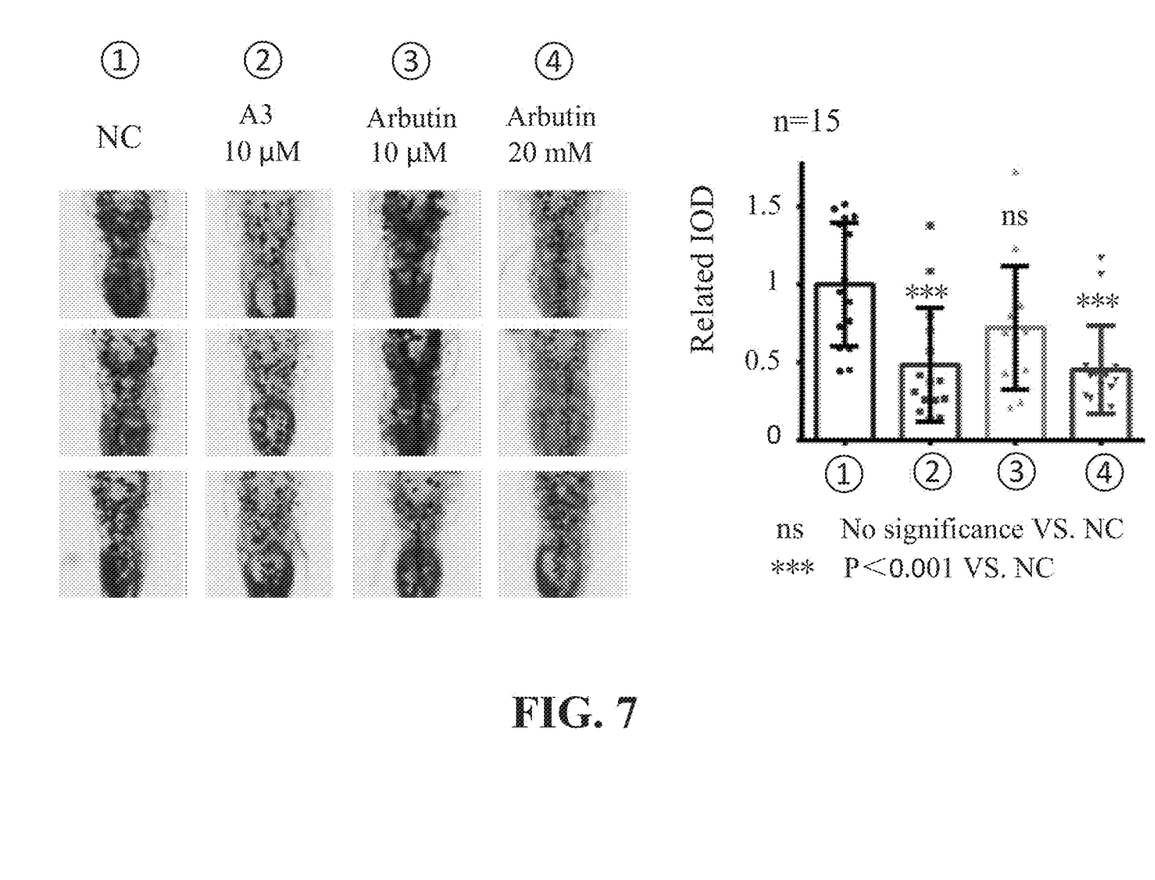
FIG. 7 shows an impact of a drug treatment on melanin production in a back of zebrafish (treatment time: 4 days)
Figure 8:
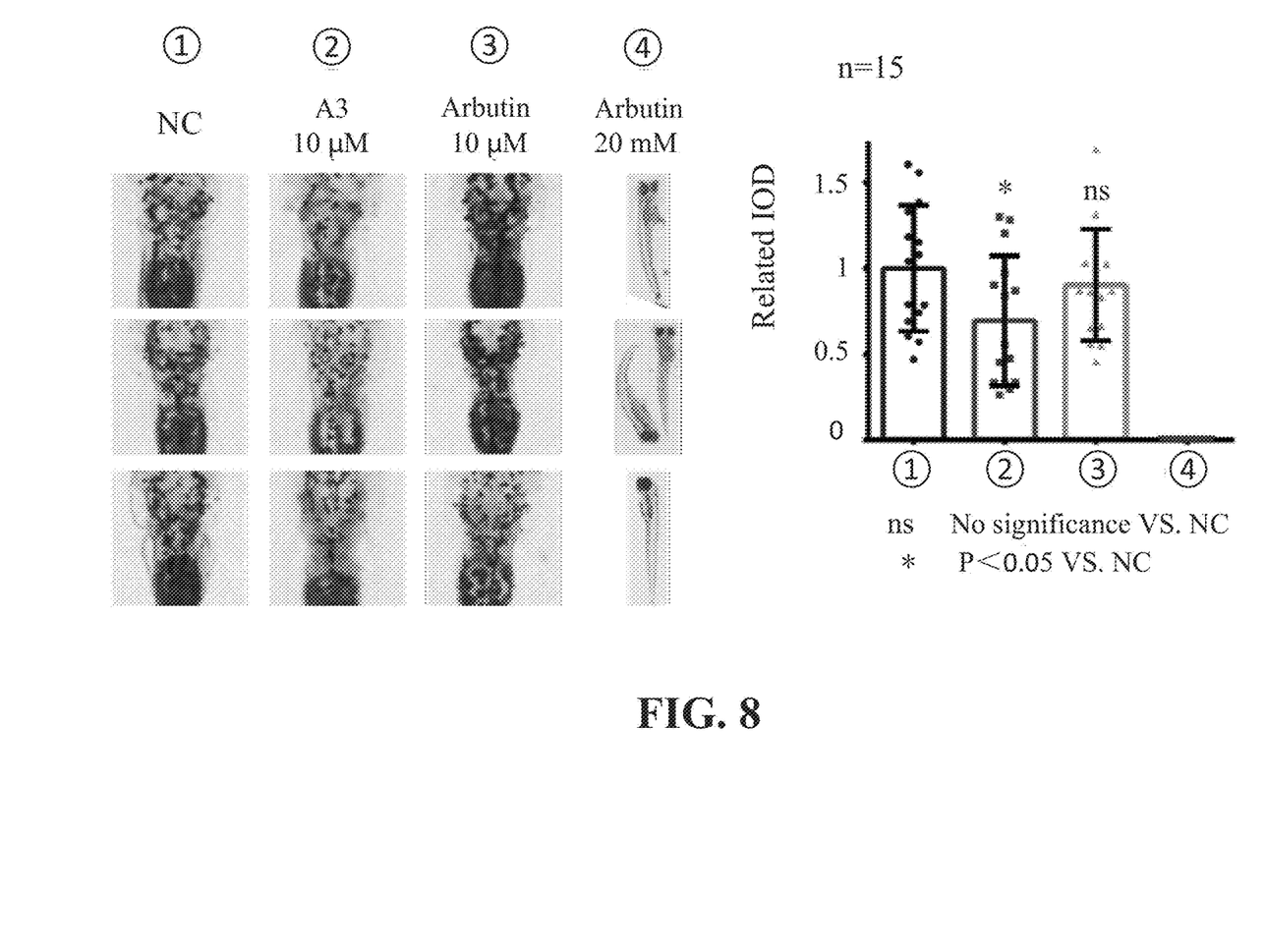
FIG. 8 shows an impact of a drug treatment on melanin production in a back of zebrafish (treatment time: 5 days)

Results are shown in FIG. 3, and it can be seen that the molecule A3 has a significant inhibitory effect on TYR in the cell line MNT-1, and the inhibitory effect of the molecule A3 on TYR in the cell line MNT-1 is enhanced with the increase of a final concentration of the molecule A3.

Test Example 3: Zebrafish Experiment

Cultivation conditions for zebrafish and fish eggs: a temperature: 28° C.±1° C.; light: irradiation with a fluorescent lamp; and a light/dark cycle: 14 h light/10 h dark.

1. A specific experimental method was as follows:
   (1) In the afternoon of day 1, fish mating was conducted to produce 800 to 1,000 fish eggs in a same batch. Experimental groups: an untreated group (negative control), a TYR-4 drug group A3 (10 μM), an arbutin group 1 (10 μM), and an arbutin group 2 (20 mM).
   (2) In the morning of day 2, fish eggs were collected and dispensed in a 24-well plate with about 10 embryos per well, where 12 wells were set for each treatment group, that is, about 120 embryos were adopted for each treatment group. In the afternoon of day 2, water was replaced by an E3 medium including a sample in a corresponding experimental group.
   (3) Every morning thereafter, the original medium was replaced by a fresh E3 medium including a sample in a corresponding experimental group.
   (4) After fish came out from an egg membrane, the egg membrane was removed, the plate was washed twice with an E3 medium, and an E3 medium including a sample in a corresponding experimental group was added, where a date on which the fish came out from the egg membrane was recorded as day 0.
   (5) From day 1 to day 5, after a medium was changed every morning, 15 fish were randomly selected from each experimental group and tested under a stereo microscope to measure a gray value of a back. Survival rates of zebrafish under different drug treatments were counted.

Measurement results of gray values of backs are shown in FIG. 4 to FIG. 8, and it can be seen that the molecule A3 has a significant inhibitory effect on melanin production in zebrafish, and at a same concentration, the molecule A3 exhibits a better effect than common whitening agents such as arbutin on the market.

Figure 9:
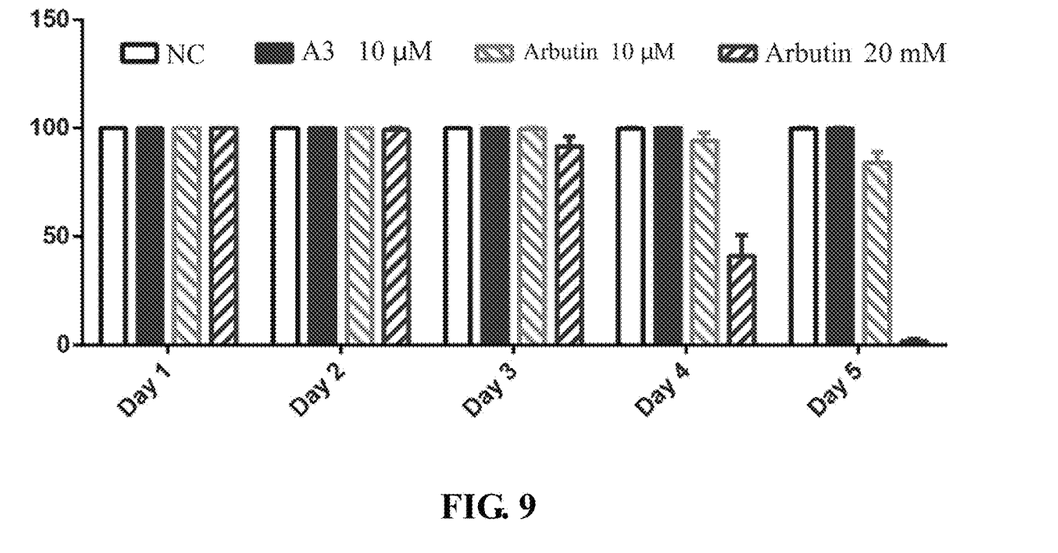
FIG. 9 is a statistical chart illustrating survival rates of zebrafish under different drug treatments.

Survival rates of zebrafish under different drug treatments are shown in FIG. 9, and it can be seen that death occurs on day 3 in the arbutin group 2 (20 mM), death occurs on day 4 in the arbutin group 1 (10 μM), a survival rate of the arbutin group 1 (10 μM) is about 80% on day 5, and zebrafish basically dies on day 5 in the arbutin group 2 (20 mM), indicating that arbutin exhibits a specified toxic effect for zebrafish at an experimental concentration and the molecule A3 does not have any toxic and side effects and does not cause death at an effective concentration.

2. After photographing was completed on day 5, 100 zebrafish were taken from each group (only 80 to 90 live fish were left in the 10 μM arbutin group), transferred to a 1.5 mL EP tube, and washed twice with pure water, then 500 μL of 1 M Tris-HCl with a pH of 8.0 was added, ultrasonic lysis was conducted on ice (40% power, on 3 s/off 2 s per cycle, and ultrasonic time: 10 min), and a resulting lysis system was centrifuged at 12,000 rpm and 4° C. for 15 min to obtain a melanin precipitate.

Figure 10:
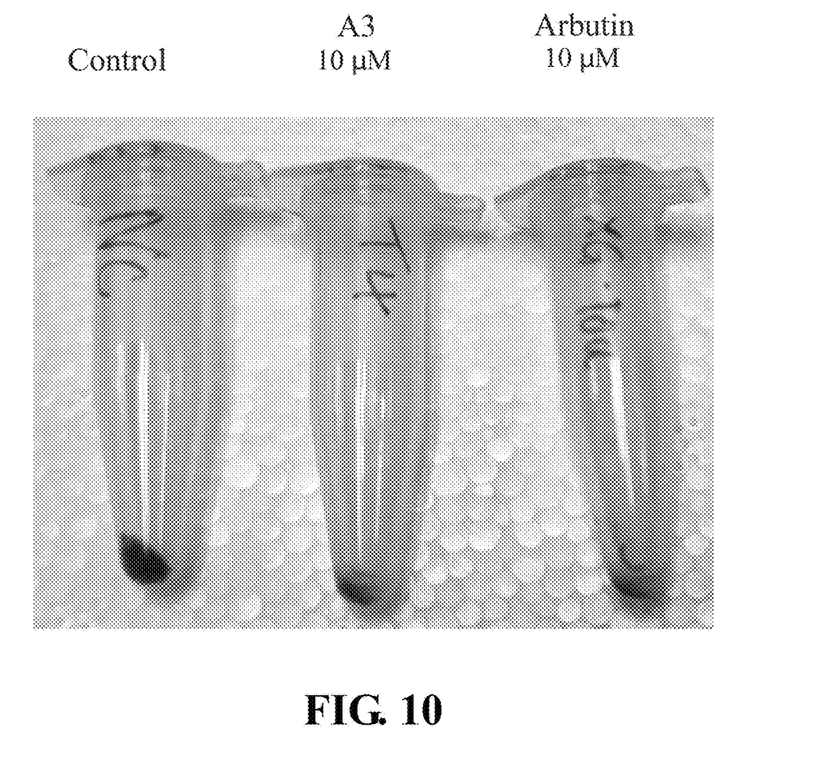
FIG. 10 shows melanin precipitates in zebrafish under drug treatments (treatment time: 5 days)

Results are shown in FIG. 10, and it can be seen that the untreated group (negative control, left panel in FIG. 10) has the largest melanin precipitate amount, and the TYR-4 drug group A3 (10 μM, middle panel in FIG. 10) and the arbutin group 1 (10 μM, right panel in FIG. 10) have similar melanin precipitate amounts, which both are significantly smaller than the melanin precipitate amount in the untreated group.

Test Example 4: Performance Test

The cytotoxicity, TYR-inhibiting efficiency, and solubility of the molecule A3 were tested. Test results are shown in Table 2.

TABLE 2

Performance test results

| | Relative molecular mass | Cytotoxicity | TYR-inhibiting efficiency | Solubility |
|---|---|---|---|---|
| A3 | 523.1889 | IC50 > 200 μM | EC50 < 10 μM | >523 mg/ml (in DMSO) |

The PROTAC molecule of the present application can significantly reduce the production of melanin by degrading human TYR. At a cellular level, an inhibition level of the PROTAC molecule for human TYR reaches less than or equal to 1 μmol/L. When zebrafish embryos and juvenile fish each are treated with the PROTAC molecule at a concentration of 1 μmol/L, the PROTAC molecule is significantly different from the positive control in terms of melanin production. The PROTAC molecule of the present application has excellent solubility and safety ($IC_{50}$>200 μM) and a low effective concentration (1 μM to 10 μM). In the cell and zebrafish experiments, the PROTAC molecule exhibits no toxic and side effects at a concentration allowing a desired effect.

Test Example 5: Degradation Pathway Detection

A molecular mechanism of the PROTAC molecule to degrade a target protein is as follows: molecular elements at two ends of the PROTAC molecule bind to the target protein and an ubiquitin ligase, respectively, such that the target protein is ubiquitinated and thus degraded by a proteasome. A proteasome inhibitor MG132 was used to determine whether an impact of the PROTAC molecule on a protein level of TYR was based on a proteasome degradation pathway.

A specific treatment method included the following steps:
(1) MNT-1 cells were plated on a 6-well plate and allowed to grow adherently until a cell confluency was 80%.
(2) The cells were treated according to the following groups:
  (a) a normal control group; (b) a 1 μM A3 treatment group; (c) a 10 μM A3 treatment group; (d) a 10 μM MG132 treatment group; (e) a 1 μM A3+10 μM MG132 treatment group; and (f) a 10 μM A3+10 μM MG132 treatment group.
(3) 24 h after a treatment, cells in each group were collected and lysed, and a resulting total protein lysate was collected and tested by WB to determine an expression level of TYR.

Figure 11:
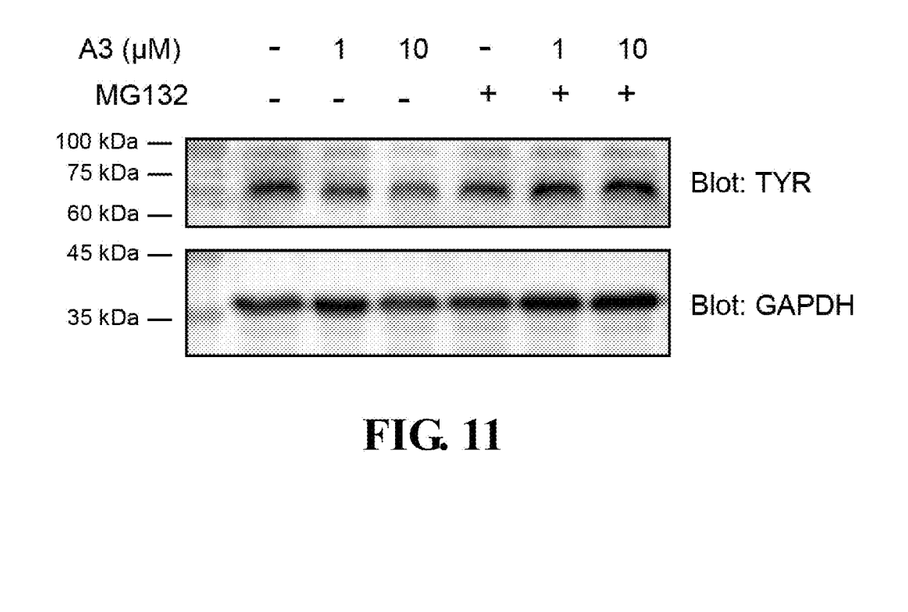
FIG. 11 shows an impact of an MG132 treatment on inhibition of A3.

Results are shown in FIG. 11, and it can be seen that a degradation effect of the PROTAC molecule A3 on TYR is significantly inhibited after MG132 is added, indicating that the degradation of the PROTAC molecule A3 on TYR is indeed allowed through a proteasome pathway.

Finally, it should be noted that the examples above are provided merely to describe the technical solutions of the present application, rather than to limit the protection scope of the present application. Although the present application is described in detail with reference to preferred examples, a person of ordinary skill in the art should understand that modifications or equivalent replacements may be made to the technical solutions of the present application without departing from the spirit and scope of the technical solutions of the present application.

The invention claimed is:

1. A proteolysis-targeting chimera (PROTAC) molecule, wherein a structural formula of the PROTAC molecule is any one selected from the group consisting of formulas (II) to (IV):

formula (II)

wherein $R_1$ is H or OH, n is 2 to 8, and Y is $CH_2$ or CO;

formula (III)

wherein $R_1$ is H or OH, n is 2 to 8, X is O, and Y is $CH_2$ or CO; and formula (IV)

wherein $R_1$ is H or OH, n is 2 to 8, and Y is $CH_2$ or CO.

* * * * *